United States Patent
Wu et al.

(10) Patent No.: US 10,563,322 B2
(45) Date of Patent: Feb. 18, 2020

(54) METHOD FOR PREPARING REGENERATED CELLULOSE FIBERS HAVING ANTI-BACTERIA, ANTI-MITE AND ANTI-MOULD FUNCTIONS AND THE USE THEREOF

(71) Applicant: Infinitus (China) Company Ltd., Jiangmen, Guangdong (CN)

(72) Inventors: Jiao Wu, Guangdong (CN); Chen Zhang, Guangdong (CN); Liuyun Hu, Guangdong (CN)

(73) Assignee: Infinitus (China) Company Ltd., Jiangmen, Guangdong (CN)

( * ) Notice: Subject to any disclaimer, the term of this patent is extended or adjusted under 35 U.S.C. 154(b) by 0 days.

(21) Appl. No.: 15/760,845

(22) PCT Filed: Jan. 4, 2018

(86) PCT No.: PCT/CN2018/071364
§ 371 (c)(1),
(2) Date: Mar. 16, 2018

(87) PCT Pub. No.: WO2019/127633
PCT Pub. Date: Jul. 4, 2019

(65) Prior Publication Data
US 2019/0203381 A1 Jul. 4, 2019

(30) Foreign Application Priority Data
Dec. 29, 2017 (CN) .......................... 2017 1 1481693

(51) Int. Cl.
*D01F 1/10* (2006.01)
*A01N 25/10* (2006.01)
*D01F 2/08* (2006.01)
*A01N 65/22* (2009.01)
*B01J 13/14* (2006.01)
*A01N 65/10* (2009.01)

(52) U.S. Cl.
CPC ............. *D01F 1/103* (2013.01); *A01N 25/10* (2013.01); *A01N 65/10* (2013.01); *A01N 65/22* (2013.01); *B01J 13/14* (2013.01); *D01F 2/08* (2013.01)

(58) Field of Classification Search
CPC ........... D01F 1/103; D01F 2/08; A01N 25/10; A01N 65/22; A01N 65/10; B01J 13/14
See application file for complete search history.

(56) References Cited

U.S. PATENT DOCUMENTS

2008/0076313 A1* 3/2008 Uitenbroek .......... C11D 17/049
442/327

FOREIGN PATENT DOCUMENTS

| CN | 1063512 | A | 8/1992 |
|---|---|---|---|
| CN | 1730738 | A | 2/2006 |
| CN | 1995498 | A | 7/2007 |
| CN | 101050560 | A | 10/2007 |
| CN | 101168867 | A | 4/2008 |
| CN | 102926013 | A | 2/2013 |
| CN | 104005110 | A | 8/2014 |
| CN | 1063512 | * | 3/2015 |
| CN | 104593893 | A | 5/2015 |
| CN | 104746162 | A | 7/2015 |
| CN | 105113033 | A | 12/2015 |
| CN | 105442073 | A | 3/2016 |
| CN | 105797660 | A | 7/2016 |
| CN | 105926077 | A | 9/2016 |
| CN | 107502966 | * | 12/2017 |
| CN | 107502966 | A | 12/2017 |
| JP | H11235388 | | 8/1999 |
| JP | 2011-505435 | | 2/2011 |

OTHER PUBLICATIONS

Young (Wood and Fiber (1978)10(2; 112-119).*
Wu et al., Chinese medicine anti-microbial & anti-mite viscose fibers prepared by microcapsule technology and its properties. Synthetic Fiber in China. 2017;46(1):20-23.

* cited by examiner

Primary Examiner — Shirley V Gembeh
(74) Attorney, Agent, or Firm — Wolf, Greenfield & Sacks, P.C.

(57) ABSTRACT

The present invention provides a method for preparing regenerated cellulose fibers having anti-bacteria, anti-mite and anti-mould functions from a fennel extract, a *Litsea cubeba* extract, and a thyme essential oil. The present invention also relates to the use of the regenerated cellulose fiber prepared by the above method in the field of anti-bacteria, anti-mite and mildew-resistant fabrics. The invention solves the technical defect that regenerated cellulose fibers have a single function and has poor anti-mite and anti-mould effects in the prior art.

10 Claims, No Drawings

METHOD FOR PREPARING REGENERATED CELLULOSE FIBERS HAVING ANTI-BACTERIA, ANTI-MITE AND ANTI-MOULD FUNCTIONS AND THE USE THEREOF

RELATED APPLICATIONS

This Application is a national stage filing under 35 U.S.C. § 371 of international patent application Serial No. PCT/CN2018/071364, filed Jan. 4, 2018, entitled "A METHOD FOR PREPARING REGENERATED CELLULOSE FIBERS HAVING ANTI-BACTERIA, ANTI-MITE AND ANTI-MOULD FUNCTIONS AND THE USE THEREOF," which claims priority to Chinese patent application number 201711481693.0, filed Dec. 29, 2017, the entire disclosure of each of which is incorporated by reference herein in its entirety.

TECHNICAL FIELD

The present invention relates to the technical field of preparation of functional regenerated cellulose fibers, in particular to a method for preparing regenerated cellulose fibers having anti-bacteria, anti-mite and anti-mould functions from a fennel extract, a *Litsea cubeba* extract, and a thyme essential oil as raw materials.

BACKGROUND OF THE INVENTION

Most regenerated cellulose fibers in China are ordinary types. With the improvement of people's living standard and the continuous enhancement of health and environmental protection awareness, it is a general trend to promote the development of healthy, environment-friendly and green functional regenerated cellulose fibers.

Mites are very closely related to human health, and the harms to human body are mainly reflected in aspects such as parasitism, sting, poisonous sting, blood-sucking, allergic diseases, transmission of diseases.

Bacteria and fungi are widespread in nature and their presence can have a number of detrimental effects on textiles, such as fiber degradation, production of ugly colors and unpleasant odors, etc. When moldy and heavily bacterial textiles are contacted, they can cause illness and endanger human health.

A Chinese patent CN201610494383.1 discloses a regenerated cellulose fiber with anti-bacteria, anti-mite and anti-mould functions and a preparation method thereof. In the technology of the patent, the preparation method comprises the following steps of: 1) preparing a cassia seed (*Semen Cassiae Obtusifoliae*)-houttuynia cordata (*Herba Houttyniae Cordatae*) microcapsule; 2) preparing a viscose spinning dope, wherein a viscose is prepared by mixing the bitter wood (*Picrasma quassioides* (d.din) benn.) pulp with other pulps selected from the group consisting of one or more of wood pulp, cotton pulp and bamboo pulp, in order to obtain the viscose spinning dope; 3) preparing a blended spinning dope, wherein the blended spinning dope is prepared by blending the cassia seed (*Semen Cassiae Obtusifoliae*)-houttuynia cordata (*Herba Houttyniae Cordatae*) microcapsule and the viscose spinning dope to prepare the blended spinning dope; and 4) spinning and performing a post-treatment, wherein the blended spinning dope is spun through a coagulation bath into a bundle, and the product is obtained by a post-treatment. In this technology, a microcapsule preparation technology and a (bitter wood) pulp preparation technology are used. The production process is complex, the production efficiency is low, and the production cost is high. Especially, a solvent method is used to extract celluloses when preparing the bitter wood pulp, which not only results in a high production cost, but also the difficulty to recover ionic liquids, further increasing the cost. Moreover, with increasing the addition amount of functional components, the physical and mechanical properties of the fibers decrease.

In the prior art, such as application numbers CN200710190764.1, CN200710014654.X, CN200510044-541.5, CN200610022614.5, CN201410187341.4, CN2015-10663207.1, CN201510998349.3, CN201510109483.3, there are problems such as single functions, poor anti-mite and anti-mould effects of regenerated cellulose fibers. With the improvement of people's living standards, regenerated cellulose fibers with anti-bacteria, anti-mite, and anti-mould functions has become the goal and direction that are pursued by a skilled person in the fiber art.

Fennel (*Fructus Foeniculi*) is acrid flavored, warm in nature, and has efficacies of eliminating cold to stop pain and relieving the gastric disorder and regulating vital energy. Active ingredients such as anisole in fennel have good antibacterial and anti-mite effects. They have good inhibitory effects on *Escherichia coli* and dysentery bacilli etc. and good anti-mite effects. *Litsea cubeba* is acrid flavored, faintly bitter, perfumed, nontoxic and has efficacies of antiasthma, anti-anaphylaxis, anti-bacteria, and anti-viruses. A plant essential oil obtained from thyme (*Thymus mongolicus Ronn.*) mainly consists of thymol and has strong efficacies of killing bacteria, mites and molds. The essential oil molecules can kill pathogens and bacteria. Those essential oil molecules entering into a human body can enhance the immunity of the human body. The essential oil molecules have efficacies of anti-bacteria, anti-inflammation, healing, deodorization and anti-mite on a dermal system and also efficacies of anti-bacteria, anti-viruses, anti-molds and anti-mite on an immune system.

SUMMARY OF THE INVENTION

The present invention solves the above problems by combining the excellent properties of fennel, *Litsea cubeba* and thyme and provides a method for preparing functional regenerated cellulose fibers from thyme, fennel, and *Litsea cubeba* as raw materials, achieving the following technique effects:

(1) As compared with the prior art, the preparation method of the invention has the advantages of being a reliable and simple production process, a high production efficiency and a low production cost, and fibers have greatly improved physical and mechanical properties and are harmless to human health.

(2) The plant multi-functional regenerated cellulose fiber prepared by the invention has multiple functions of anti-bacteria, anti-mite and anti-mould effects etc. . . . The fiber has a repellent rate of 85% or more and a inhibitory rate of 85% or more against mites (GB/T24346-2009 "Textiles-Evaluation for anti-mite activity"). The anti-mould level can reach 0 level and above (GB/T24346-2009 "Textiles-Evaluation for anti-mould activity"). The antibacterial activity value is 2.2-2.8, and the bactericidal activity value is 0.3-0.7.

(3) The plant regenerated cellulose fiber prepared by the invention has the advantages of good physical and mechanical properties, a high strength, a small variation coefficient of strength, and a high wet modulus, and has a fiber degree of polymerization of 450-515, a dry breaking strength of 3.89-4.52 cN/dtex, a variation coefficient of dry strength of 11.2-13.6%, a wet breaking strength of 2.68-3.11 cN/dtex, a hooking strength of 0.90-1.22 cN/dtex and a wet modulus of 0.48-0.75 cN/dtex.

To solve the above technical problems, the following technical solutions are adopted:

A method for preparing plant regenerated cellulose fibers having anti-bacteria, anti-mite and anti-mould functions, comprising the steps of:

(1) preparing a composite slurry;

(2) blending the composite slurry and a denatured cellulose spinning dope to prepare a blended spinning dope; and (3) spinning the blended spinning dope and performing a post-treatment.

Preferably, the composite slurry is prepared by the following process:

i) blending a fennel (*Fructus Foeniculi*) extract and a *Litsea cubeba* extract to obtain a blended powder;

ii) mixing the blended powder obtained in step i) with a thyme (*Thymus mongolicus Ronn.*) essential oil to prepare an oily blended powder slurry and further emulsifying to obtain an emulsion;

iii) reacting the emulsion obtained in step ii) with a urea-formaldehyde resin prepolymer to obtain the composite slurry.

More preferably, in step i) of preparation of the composite slurry, the fennel extract and the *Litsea cubeba* extract are blended in a mass ratio of 1:(0.5-1.5), and the particle size D90 of the blended powder is ≤51.568 μm.

More preferably, in step ii) of preparation of the composite slurry, the mass ratio of the blended powder to the thyme essential oil is (5-10):1.

More preferably, in step ii) of preparation of the composite slurry, the emulsifying is emulsifying by adding the oily blended powder slurry into an aqueous system containing 0.5-1.5% of styrene-maleic anhydride sodium salt, wherein the mass ratio of the oily blended powder slurry to the aqueous system is 1:(2-5), and the particle size D90 of emulsion is ≤2.038 μm.

More preferably, in step iii) of preparation of the composite slurry, the emulsion is reacted with the urea-formaldehyde resin prepolymer at 70-80° C. with stirring, and the ratio of the total mass of the fennel extract, the *Litsea cubeba* extract and the thyme essential oil in the emulsion to the mass of the urea-formaldehyde resin prepolymer is (1-3):1. The particle size D90 of the composite slurry is ≤2.562 μm, and the solid content is 20%-40%.

Preferably, the denatured cellulose spinning dope of the step (2) is prepared by first preparing a viscose dope from a cellulose pulp having a polymerization degree of 800 to 1000 as a raw material, and then adding a denaturant, a polyoxyethylene compound, wherein the ratio of the addition amount of the denaturant to the mass of the α-cellulose in the viscose dope is 0.1-1.0%. The denatured cellulose spinning dope has a viscosity of 60-96 s and the degree of esterification of 65-85.

Preferably, the mass ratio of the composite slurry in the blended spinning dope of the step (2) to the α-cellulose in the denatured cellulose spinning dope is 4.0% to 10.0%.

Preferably, the spinning in step (3) uses a coagulation bath at a coagulation temperature of 20 to 40° C. and the coagulation bath composition comprises 5.0 to 8.0% of sulfuric acid, 0.5 to 1.0% of aluminum sulfate, 10.0%-16.0% of sodium sulfate, 0.1-0.5% of the polyoxyethylene compound, the balance being water.

Preferably, the post-treatment of step (3) comprises desulfurization, oil bathing, water washing and drying by baking.

The fennel extract and the *Litsea cubeba* extract involved in the above steps are commercially available or prepared by using well-known techniques. The conventional preparation method is as follows:

1) taking effective parts of the fennel or *Litsea cubeba* plant, cleaning, washing, and drying at 90-110° C.;

2) crushing the dried material, adding 8-10× mass of water and extracting at 90-100° C. for 2-4 hours;

3) filtrating, spray-drying the extract via a granulator to obtain extract particles.

The specifications of the obtained fennel extract and *Litsea cubeba* extract are 1 kg the fennel extract and *Litsea cubeba* extract from 10 kg the traditional Chinese drug fennel plant or *Litsea cubeba* plant, respectively, wherein the total active ingredient content is ≥30%.

A thyme essential oil involved in the above steps is obtained by techniques well known in the art such as water steam distillation and solvent extraction.

The urea-formaldehyde resin prepolymer involved in the above steps is prepared according to well known techniques. A conventional preparation method is as follows: mixing the urea, glutaraldehyde and distilled water homogeneously, wherein the ratio of urea to glutaraldehyde is (2-3):1, and adding triethanolamine or sodium hydroxide to adjust the pH to 8-9 and then heating to 60-70° C. for reaction, adding PVA after the solution becomes clear, wherein PVA is added in an amount of 2.0%-8.0% of urea content, decreasing the temperature to 75-85° C., reacting for 30~50 min at a constant temperature, and then using sodium hydroxide to adjust the pH of the system to neutral, and cooling to 40-45° C. for future use.

The present invention also relates to use of the regenerated cellulose fiber obtained by the above preparation method in anti-bacteria, anti-mite and mildew-resistant fabrics.

As compared with the prior art, the present invention adopts the above technical solutions and has the following beneficial effects:

(1) As compared with the prior art, the preparation method of the invention has the advantages of being a reliable and simple production process, a low production cost, avoiding environmental pollution by substitution of zinc sulfate for aluminum sulfate in the preparation process, greatly improved physical and mechanical properties of the fiber, achieving the combination of multiple plant functions in fibers, a good durability, and a good washability (>50 times). Moreover, functional components come from nature and are not harmful to human health.

(2) The plant multi-functional regenerated cellulose fiber prepared by the invention has multiple functions of anti-bacteria, anti-mould and anti-mite effects etc. . . . The fiber has a repellent rate of 85% or more and a inhibitory rate of 85% or more against mites. The anti-mould level can reach 0 level and above. The antibacterial activity value is 2.2-2.8, and the bactericidal activity value is 0.3-0.7.

(3) The plant multi-functional regenerated cellulose fiber prepared by the invention has advantages of good physical and mechanical properties, a high strength, a small variation coefficient of strength, a high wet modulus, and has a fiber degree of polymerization of 450-515, a dry breaking strength of 2.89-3.52 cN/dtex, a variation coefficient of dry strength of 11.2-13.6%, a wet strength of 1.68-2.11 cN/dtex, a hooking strength of 0.90-1.22 cN/dtex and a wet modulus of 0.38-0.55 cN/dtex.

Description of Anti-Bacteria, Anti-Mould, and Anti-Mite Evaluation:

| class | Detection item | Requirements | Detection method |
|---|---|---|---|
| anti-bacteria, anti-mould, anti-mite indicators | anti-bacterial effects and safety evaluation after dissolution | 1. antibacterial grades after washing for 0-20 time(s) with water<br>2. inhibition zone widths after washing for 1 time | the antibacterial test is found in the FZ/T 73023 shaking method; the inhibition zone detection: FZ/T 73023 Halo test |
| | anti-mite effect evaluation | repellent rates or inhibitory rates after washing for 0 time and 10 times | GB/T 24253 repellent method or inhibition method |
| | anti-mould effect evaluation | anti-mould levels after washing for 0 time and 20 times | GB/T24346 Petri dish method |

The invention also relates to the use of fennel (*Fructus Foeniculi*), *Litsea cubeba* and a \ thyme essential oil as functional modifier additives for the preparation of a regenerated cellulose fiber having anti-bacteria, anti-mite and anti-mould functions.

According to the present invention, it has been found that a regenerated cellulose fiber having anti-bacteria, anti-mite and anti-mould functions can be prepared by using a combination of fennel, *Litsea cubeba* and thyme as raw material sources. The obtained regenerated cellulose fiber has a high repellent rate and inhibitory rate against mites, and the anti-mold level can reach 0 level. Moreover, the fiber also has excellent bacteriostatic and bactericidal activities. In addition, the regenerated cellulose fiber obtained by the invention has very good physical and mechanical properties, a high strength, a small variation coefficient of strength and a high wet modulus, which are of great significance to the development of China's textile industry and people's health.

EXAMPLES

In the following, preferred embodiments of the present invention are described. It should be understood that the preferred embodiments described herein are only for illustrating and explaining the present invention, and not intended to limit the present invention.

Example 1

A method for preparing regenerated cellulose fibers having anti-bacteria, anti-mite and anti-mould functions with a specification of 1.11 dtex×38 mm, comprising the steps of:

1. The Preparation Step of a Composite Slurry 1) a fennel extract and a *Litsea cubeba* extract were mixed, crushed, ground to obtain a blended powder of the two for future use, wherein the mass ratio of the fennel extract to the *Litsea cubeba* extract in blended powder was 1:0.5, and the particle size D90 of the powder was 1.256 μm.

2) The above prepared blended powder and a thyme essential oil were blended homogeneously, so that the surface of the blended powder was covered with a layer of the thyme essential oil to prepare an oily blended powder slurry, wherein the mass ratio of the blended powder to the thyme essential oil was 5:1.

The above oily blended powder slurry was added into an emulsifier, a styrene maleic anhydride sodium salt aqueous system having styrene maleic anhydride sodium salt content of 0.5%, forming O/W emulsion, wherein the mass ratio of the oily blended powder slurry to the aqueous system was 1:5, and the particle size D90 of the emulsified emulsion was 1.565 μm.

3) Preparation of the composite slurry. The oily blended powder slurry emulsion was added to a urea-formaldehyde resin prepolymer, reacted at 70-80° C. with sufficiently stirring, so that the urea-formaldehyde resin prepolymer crossly link to prepare a plant composite slurry, which is composed of the oily blended powder slurry emulsion obtained using thyme, fennel and *Litsea cubeba* as plant sources being a capsule core and the urea-formaldehyde resin being a capsule wall, wherein the ratio of the total mass amount of the fennel extract, the *Litsea cubeba* extract and the A thyme essential oil to the mass of the urea-formaldehyde resin prepolymer was 1:1, the particle size D90 of the multi-functional composite slurry was 2.216 μm, and the solid content was 20.1%.

2. The Step for Preparing a Blended Spinning Dope by Blending the Composite Slurry and a Denatured Cellulose Spinning Dope 1) The Step for Preparing a Denatured Cellulose Spinning Dope Cellulose pulps were used as raw materials. A viscose dope was prepared through a viscose preparation process, and a denaturant was added into the viscose dope for denaturation to prepare a denatured cellulose spinning dope. The polymerization degree of the cellulose pulps was 800. The denaturant used was a polyoxyethylene compound and the ratio of the addition amount to the mass of the α-cellulose in the viscose dope was 0.1%. The viscosity of the denatured cellulose spinning dope was 60 s and the degree of esterification was 65.

2) The Step for Blending to Prepare a Blend Spinning Dope

The composite slurry prepared in step 1 was added to the denatured cellulose spinning dope prepared in step 2 through a pre-spinning injection system, wherein the pre-spinning injection system comprised a filtering device, a metering device and a mixing device to achieve the filtration of the plant composite slurry, precise metering, and homogeneously mixing with the denatured cellulose spinning dope. The mass ratio of the composite slurry to the α-cellulose in the denatured cellulose spinning dope was 4.0%. The particle size of the particles allowed to pass through the filter device of the pre-spinning injection system was 2.658 μm. The mixing device consisted of a dynamic mixer, and the mixing time was 30 s.

3. Spinning and Post-Treatment

The blended spinning dope was spun through a adjusted coagulation bath, and the primary tow was drafted to obtain a shaped tow. The resulting tow was cut, subjected to a mild desulfurization process, transferred to an oil bath and refining baths such as for water washing. A plant regenerated cellulose fiber having anti-bacteria, anti-mite and anti-mould functions was obtained after drying.

The coagulation bath temperature was 20° C. The coagulation bath composition consisted of 5.0% of sulfuric acid, 0.5% of aluminum sulphate, 10.0% of sodium sulphate and 0.1% of polyoxyethylene compounds with the balance being water.

The fiber had a repellent rate of 85% and a inhibitory rate of 85% against mites. The anti-mould level could reach 1 level. The antibacterial activity value was 2.2, and the bactericidal activity value was 0.3. The fiber had a fiber degree of polymerization of 515, a dry breaking strength of 3.52 cN/dtex, a variation coefficient of dry strength of 11.2%, a wet strength of 2.11 cN/dtex, a hooking strength of 1.22 cN/dtex and a wet modulus of 0.55 cN/dtex.

Example 2

A method for preparing plant regenerated cellulose fibers having anti-bacteria, anti-mite and anti-mould functions with a specification of 1.33 dtex×38 mm, comprising the steps of:

1. The Preparation Step of a Composite Slurry 1) a fennel extract and a *Litsea cubeba* extract were mixed, crushed, ground to obtain a blended powder of the two for future use, wherein the mass ratio of the fennel extract to the *Litsea cubeba* extract in blended powder was 1:0.75, and the particle size D90 of the blended powder was 1.321 μm.

2) The above prepared blended powder and a thyme essential oil were blended homogeneously, so that the surface of the blended powder was covered with a layer of the thyme essential oil to prepare an oily blended powder slurry, wherein the mass ratio of the blended powder to the thyme essential oil was 6:1.

The above oily blended powder slurry was added into an emulsifier, a styrene maleic anhydride sodium salt aqueous system having styrene maleic anhydride sodium salt content of 0.65%, forming O/W emulsion, wherein the mass ratio of the oily blended powder slurry to the aqueous system was 1:4, and the particle size D90 of the emulsified emulsion was 1.663 μm.

3) Preparation of the composite slurry. The oily blended powder slurry emulsion was added to a urea-formaldehyde resin prepolymer, reacted at 70-80° C. with sufficiently stirring, so that the urea-formaldehyde resin prepolymer cross linkly to prepare a plant composite slurry, which is composed of the oily blended powder slurry emulsion obtained using thyme, fennel and *Litsea cubeba* as plant sources being a capsule core and the urea-formaldehyde resin being a capsule wall, wherein the ratio of the total mass amount of the fennel extract, the *Litsea cubeba* extract and the A thyme essential oil to the mass of the urea-formaldehyde resin prepolymer was 1.2:1, the particle size D90 of the multi-functional composite slurry was 2.312 μm, and the solid content was 26.7%.

2. The Step for Preparing a Blended Spinning Dope by Blending the Composite Slurry and a Denatured Cellulose Spinning Dope 1) The Step for Preparing a Denatured Cellulose Spinning Dope Cellulose pulps were used as raw materials. A viscose dope was prepared through a viscose preparation process, and a denaturant was added into the viscose dope for denaturation to prepare a denatured cellulose spinning dope. The polymerization degree of the cellulose pulps was 826. The denaturant used was a polyoxyethylene compound and the ratio of the addition amount to the mass of the α-cellulose in the viscose dope was 0.26%. The viscosity of the denatured cellulose spinning dope was 68 s and the degree of esterification was 73.

2) The Step for Blending to Prepare a Blend Spinning Dope

The composite slurry prepared in step 1 was added to the denatured cellulose spinning dope prepared in step 2 through a pre-spinning injection system, wherein the pre-spinning injection system comprised a filtering device, a metering device and a mixing device to achieve the filtration of the plant composite slurry, precise metering, and homogeneously mixing with the denatured cellulose spinning dope. The mass ratio of the composite slurry to the α-cellulose in the denatured cellulose spinning dope was 5.8%. The particle size of the particles allowed to pass through the filter device of the pre-spinning injection system was 2.756 μm. The mixing device consisted of a static mixer, and the mixing time was 78 s.

3. Spinning and Post-Treatment

The blended spinning dope was spun through an adjusted coagulation bath, and the primary tow was drafted to obtain a shaped tow. The resulting tow was cut, subjected to a mild desulfurization process, transferred to an oil bath and refining baths such as for water washing. A plant regenerated cellulose fiber having anti-bacteria, anti-mite and anti-mould functions was obtained after drying.

The coagulation bath temperature was 26° C. The coagulation bath composition consisted of 5.2% of sulfuric acid, 0.62% of aluminum sulphate, 10.0% of sodium sulphate and 0.15% of polyoxyethylene compounds with the balance being water.

The fiber had a repellent rate of 88% and an inhibitory rate of 87% against mites. The anti-mould level could reach 1 level. The antibacterial activity value was 2.4, and the bactericidal activity value was 0.4. The fiber had a fiber degree of polymerization of 502, a dry breaking strength of 3.44 cN/dtex, a variation coefficient of dry strength of 12.1%, a wet strength of 2.02 cN/dtex, a hooking strength of 1.15 cN/dtex and a wet modulus of 0.52 cN/dtex.

Example 3

A method for preparing regenerated cellulose fibers having anti-bacteria, anti-mite and anti-mould functions with a specification of 1.56 dtex×38 mm, comprising the steps of:

1. The Preparation Step of a Composite Slurry 1) a fennel extract and a *Litsea cubeba* extract were mixed, crushed, ground to obtain a blended powder of the two for future use, wherein the mass ratio of the fennel extract to the *Litsea cubeba* extract in blended powder was 1:1, and the particle size D90 of the blended powder was 1.412 μm.

2) The above prepared blended powder and a thyme essential oil were blended homogeneously, so that the surface of the blended powder was covered with a layer of the thyme essential oil to prepare a oily blended powder slurry, wherein the mass ratio of the blended powder to the thyme essential oil was 7:1.

The above oily blended powder slurry was added into an emulsifier, a styrene maleic anhydride sodium salt aqueous system having styrene maleic anhydride sodium salt content of 0.89%, forming O/W emulsion, wherein the mass ratio of the oily blended powder slurry to the aqueous system was 1:3, and the particle size D90 of the emulsified emulsion was 1.782 μm.

3) Preparation of the composite slurry. The oily blended powder slurry emulsion was added to a urea-formaldehyde resin prepolymer, reacted at 70-80° C. with sufficiently stirring, so that the urea-formaldehyde resin prepolymer crossly link to prepare a plant composite slurry, which is composed of the oily blended powder slurry emulsion obtained using thyme, fennel and *Litsea cubeba* as plant sources being a capsule core and the urea-formaldehyde resin being a capsule wall, wherein the ratio of the total mass amount of the fennel extract, the *Litsea cubeba* extract and the thyme essential oil to the mass of the urea-formaldehyde resin prepolymer was 1.5:1, the particle size D90 of the multi-functional composite slurry was 2.396 μm, and the solid content was 32.5%.

2. The Step for Preparing a Blended Spinning Dope by Blending the Composite Slurry and a Denatured Cellulose Spinning Dope 1) The Step for Preparing a Denatured Cellulose Spinning Dope Cellulose pulps were used as raw materials. A viscose dope was prepared through a viscose preparation process, and a denaturant was added into the viscose dope for denaturation to prepare a denatured cellulose spinning dope. The polymerization degree of the cellulose pulps was 896. The denaturant used was a polyoxyethylene compound and the ratio of the addition amount to the mass of the α-cellulose in the viscose dope was 0.51%. The viscosity of the denatured cellulose spinning dope was 76 s and the degree of esterification was 78.

2) The Step for Blending to Prepare a Blend Spinning Dope

The composite slurry prepared in step 1 was added to the denatured cellulose spinning dope prepared in step 2 through a pre-spinning injection system, wherein the pre-spinning injection system comprised a filtering device, a metering device and a mixing device to achieve the filtration of the plant composite slurry, precise metering, and homogeneously mixing with the denatured cellulose spinning dope. The mass ratio of the composite slurry to α-cellulose in the denatured cellulose spinning dope was 7.5%. The particle size of the particles allowed to pass through the filter device of the pre-spinning injection system was 2.632 μm. The mixing device consisted of a dynamic mixer and a static mixer linked in series, and the mixing time was 155 s.

3. Spinning and Post-Treatment

The blended spinning dope was spun through an adjusted coagulation bath, and the primary tow was drafted to obtain a shaped tow. The resulting tow was cut, subjected to a mild desulfurization process, transferred to an oil bath and refining baths such as for water washing. A plant regenerated cellulose fiber having anti-bacteria, anti-mite and anti-mould functions was obtained after drying.

The coagulation bath temperature was 31° C. The coagulation bath composition consisted of 6.5% of sulfuric acid, 0.76% of aluminum sulphate, 13.2% of sodium sulphate and 0.25% of polyoxyethylene compounds with the balance being water.

The fiber had a repellent rate of 92% and an inhibitory rate of 92% against mites. The anti-mould level could reach 0 level. The antibacterial activity value was 2.5, and the bactericidal activity value was 0.5. The fiber had a fiber degree of polymerization of 488, a dry breaking strength of 3.32 cN/dtex, a variation coefficient of dry strength of 12.5%, a wet strength of 1.89 cN/dtex, a hooking strength of 1.07 cN/dtex and a wet modulus of 0.45 cN/dtex.

Example 4

A method for preparing regenerated cellulose fibers having anti-bacteria, anti-mite and anti-mould functions with a specification of 1.67 dtex×38 mm, comprising the steps of:

1. The Preparation Step of a Composite Slurry 1) a fennel extract and a *Litsea cubeba* extract were mixed, crushed, ground to obtain a blended powder of the two for future use, wherein the mass ratio of the fennel extract to the *Litsea cubeba* extract in blended powder was 1:1.25, and the particle size D90 of the blended powder was 1.523 μm.

2) The above prepared blended powder and a thyme essential oil were blended homogeneously, so that the surface of the blended powder was covered with a layer of the thyme essential oil to prepare an oily blended powder slurry, wherein the mass ratio of the blended powder to the thyme essential oil was 8.5:1.

The above oily blended powder slurry was added into an emulsifier, a styrene maleic anhydride sodium salt aqueous system having styrene maleic anhydride sodium salt content of 0.5%, forming O/W emulsion, wherein the mass ratio of the oily blended powder slurry to the aqueous system was 1:2, and the particle size D90 of the emulsified emulsion was 1.905 μm.

3) Preparation of the composite slurry. The oily blended powder slurry emulsion was added to a urea-formaldehyde resin prepolymer, reacted at 70-80° C. with sufficiently stirring, so that the urea-formaldehyde resin prepolymer crossly link to prepare a plant composite slurry, which is composed of the oily blended powder slurry emulsion obtained using thyme, fennel and *Litsea cubeba* as plant sources being a capsule core and the urea-formaldehyde resin being a capsule wall, wherein the ratio of the total mass amount of the fennel extract, the *Litsea cubeba* extract and the thyme essential oil to the mass of the urea-formaldehyde resin prepolymer was 2:1, the particle size D90 of the multi-functional composite slurry was 2.443 μm, and the solid content was 36.8%.

2. The Step for Preparing a Blended Spinning Dope by Blending the Composite Slurry and a Denatured Cellulose Spinning Dope 1) The Step for Preparing a Denatured Cellulose Spinning Dope Cellulose pulps were used as raw materials. A viscose dope was prepared through a viscose preparation process, and a denaturant was added into the viscose dope for denaturation to prepare a denatured cellulose spinning dope. The polymerization degree of the cellulose pulps was 937. The denaturant used was a polyoxyethylene compound and the ratio of the addition amount to the mass of the α-cellulose in the viscose dope was 0.78%. The viscosity of the denatured cellulose spinning dope was 88 s and the degree of esterification was 81.

2) The Step for Blending to Prepare a Blend Spinning Dope

The composite slurry prepared in step 1 was added to the denatured cellulose spinning dope prepared in step 2 through a pre-spinning injection system, wherein the pre-spinning injection system comprised a filtering device, a metering device and a mixing device to achieve the filtration of the plant composite slurry, precise metering, and homogeneously mixing with the denatured cellulose spinning dope. The mass ratio of the composite slurry to α-cellulose in the denatured cellulose spinning dope was 8.9%. The particle size of the particles allowed to pass through the filter device of the pre-spinning injection system was 2.852 μm. The mixing device consisted of a dynamic mixer and a static mixer linked in series, and the mixing time was 196 s.

3. Spinning and Post-Treatment

The blended spinning dope was spun through a adjusted coagulation bath, and the primary tow was drafted to obtain a shaped tow. The resulting tow was cut, subjected to a mild desulfurization process, transferred to an oil bath and refining baths such as for water washing. A plant regenerated cellulose fiber having anti-bacteria, anti-mite and anti-mould functions was obtained after drying.

The coagulation bath temperature was 36° C. The coagulation bath composition consisted of 7.2% of sulfuric acid, 0.78% of aluminum sulphate, 13.8% of sodium sulphate and 0.32% of polyoxyethylene compounds with the balance being water.

The fiber had a repellent rate of 95% and a inhibitory rate of 94% against mites. The anti-mould level could reach 0 level. The antibacterial activity value was 2.7, and the bactericidal activity value was 0.6. The fiber had a fiber degree of polymerization of 475, a dry breaking strength of 3.09 cN/dtex, a variation coefficient of dry strength of 13.3%, a wet strength of 1.75 cN/dtex, a hooking strength of 0.98 cN/dtex and a wet modulus of 0.40 cN/dtex.

Example 5

A method for preparing regenerated cellulose fibers having anti-bacteria, anti-mite and anti-mould functions with a specification of 2.22 dtex×38 mm, comprising the steps of:

1. The Preparation Step of a Composite Slurry 1) a fennel extract and a *Litsea cubeba* extract were mixed, crushed, ground to obtain a blended powder of the two for future use, wherein the mass ratio of the fennel extract to the *Litsea cubeba* extract in blended powder was 1:1.5, and the particle size D90 of the blended powder was 1.568 μm.

2) The above prepared blended powder and a thyme essential oil were blended homogeneously, so that the surface of the blended powder was covered with a layer of the thyme essential oil to prepare a oily blended powder slurry, wherein the mass ratio of the blended powder to the thyme essential oil was 10:1.

The above oily blended powder slurry was added into an emulsifier, a styrene maleic anhydride sodium salt aqueous system having styrene maleic anhydride sodium salt content of 0.5%, forming O/W emulsion, wherein the mass ratio of the oily blended powder slurry to the aqueous system was 1:5, and the particle size D90 of the emulsified emulsion was 2.038 μm.

3) Preparation of the composite slurry. The oily blended powder slurry emulsion was added to a urea-formaldehyde resin prepolymer, reacted at 70-80° C. with sufficiently stirring, so that the urea-formaldehyde resin prepolymer crossly link to prepare a plant composite slurry, which is composed of the oily blended powder slurry emulsion obtained using thyme, fennel and *Litsea cubeba* as plant sources being a capsule core and the urea-formaldehyde resin being a capsule wall, wherein the ratio of the total mass amount of the fennel extract, the *Litsea cubeba* extract and the A thyme essential oil to the mass of the urea-formaldehyde resin prepolymer was 3:1, the particle size D90 of the multi-functional composite slurry was 2.562 μm, and the solid content was 39.9%.

2. The Step for Preparing a Blended Spinning Dope by Blending the Composite Slurry and a Denatured Cellulose Spinning Dope 1) The Step for Preparing a Denatured Cellulose Spinning Dope Cellulose pulps were used as raw materials. A viscose dope was prepared through a viscose preparation process, and a denaturant was added into the viscose dope for denaturation to prepare a denatured cellulose spinning dope. The polymerization degree of the cellulose pulps was 1000. The denaturant used was a polyoxyethylene compound and the ratio of the addition amount to the mass of the α-cellulose in the viscose dope was 1.0%. The viscosity of the denatured cellulose spinning dope was 96 s and the degree of esterification was 85.

2) The Step for Blending to Prepare a Blend Spinning Dope

The composite slurry prepared in step 1 was added to the denatured cellulose spinning dope prepared in step 2 through a pre-spinning injection system, wherein the pre-spinning injection system comprised a filtering device, a metering device and a mixing device to achieve the filtration of the plant composite slurry, precise metering, and homogeneously mixing with the denatured cellulose spinning dope. The mass ratio of the composite slurry to α-cellulose in the denatured cellulose spinning dope was 10.0%. The particle size of the particles allowed to pass through the filter device of the pre-spinning injection system was 2.968 μm. The mixing device consisted of a dynamic mixer and a static mixer linked in series, and the mixing time was 300 s.

3. Spinning and Post-Treatment

The blended spinning dope was spun through a adjusted coagulation bath, and the primary tow was drafted to obtain a shaped tow. The resulting tow was cut, subjected to a mild desulfurization process, transferred to an oil bath and refining baths such as for water washing. A plant regenerated cellulose fiber having anti-bacteria, anti-mite and anti-mould functions was obtained after drying.

The coagulation bath temperature was 40° C. The coagulation bath composition consisted of 8.0% of sulfuric acid, 1.0% of aluminum sulphate, 16.0% of sodium sulphate and 0.5% of polyoxyethylene compounds with the balance being water.

The fiber had a repellent rate of 98% and a inhibitory rate of 98% against mites. The anti-mould level could reach 0 level. The antibacterial activity value was 2.8, and the bactericidal activity value was 0.7. The fiber had a fiber degree of polymerization of 450, a dry breaking strength of 2.89 cN/dtex, a variation coefficient of dry strength of 13.6%, a wet strength of 1.68 cN/dtex, a hooking strength of 0.90 cN/dtex and a wet modulus of 0.38 cN/dtex.

It should be understood that the foregoing descriptions are merely illustrative of preferred embodiments of the present invention and are not used to limit the present invention. Although the present invention is described in detail with reference to the foregoing embodiments, it will be apparent to those skilled in the art that, the technical solutions described in the foregoing embodiments may be modified. Any modification, equivalent substitution, or improvement made without departing from the spirit and principle of the present invention shall fall within the protection scope of the present invention.

We claim:
1. A method for preparing a regenerated cellulose fiber having anti-bacterial, anti-mite and anti-mould functions, comprising the steps of:
  (1) preparing a composite slurry;
  (2) blending the composite slurry and a denatured cellulose spinning dope to prepare a blended spinning dope; and
  (3) spinning the blended spinning dope and performing a post-treatment, thereby producing the regenerated cellulose fiber,
  wherein the composite slurry is prepared by a process comprising:
  i) blending a *Fructus Foeniculi* extract and a *Litsea cubeba* extract to obtain a blended powder;
  ii) mixing the blended powder obtained in step i) with a *Thymus mongolicus Ronn* essential oil to prepare an oily blended powder slurry and further emulsifying the oily blended power slurry to obtain an emulsion; and
  iii) reacting the emulsion obtained in step ii) with a urea-formaldehyde resin prepolymer to obtain the composite slurry.

2. The method of claim 1, wherein the *Fructus Foeniculi* extract and the *Litsea cubeba* extract are blended in a mass ratio of 1:(0.5-1.5) in step i), and the particle size D90 of the blended powder is ≤1.568 μm.

3. The method of claim 1, wherein the mass ratio of the blended powder to the *Thymus mongolicus Ronn* essential oil in step ii) is (5-10):1.

4. The method of claim 1, wherein the emulsifying in step ii) is performed by adding the oily blended powder slurry into an aqueous system containing 0.5-1.5% of styrene-maleic anhydride sodium salt, wherein the mass ratio of the oily blended powder slurry to the aqueous system is 1:(2-5), and wherein the particle size D90 of emulsion is ≤2.038 μm.

5. The method of claim 1, wherein in step iii), the emulsion is reacted with the urea-formaldehyde resin prepolymer at 70-80° C. with stirring, wherein the ratio of the total mass of the *Fructus Foeniculi* extract, the *Litsea cubeba* extract and the *Thymus mongolicus Ronn* essential oil in the emulsion to the mass of the urea-formaldehyde resin prepolymer is (1-3):1, and wherein the particle size D90 of the composite slurry is ≤2.562 μm, and the solid content is 20%-40%.

6. The method of claim 1, wherein the denatured cellulose spinning dope of the step (2) is prepared by a process comprising: first preparing a viscose dope from a cellulose pulp having a polymerization degree of 800 to 1000 as a raw material, and then adding a denaturant of a polyoxyethylene compound, wherein the ratio of the addition amount of the denaturant to the mass of the α-cellulose in the viscose dope is 0.1-1.0%, the denatured cellulose spinning dope has a viscosity of 60-96 s and the degree of esterification of 65-85.

7. The method of claim 1, wherein the mass ratio of the composite slurry in the blended spinning dope of the step (2) to the α-cellulose in the denatured cellulose spinning dope is 4.0% to 10.0%.

8. The method of claim 1, wherein a coagulation bath is used in the step (3) of spinning with a coagulation temperature of 20 to 40° C. and the coagulation bath composition comprises 5.0 to 8.0% of sulfuric acid, 0.5 to 1.0% of aluminum sulfate, 10.0%-16.0% of sodium sulfate, 0.1-0.5% of the polyoxyethylene compound, the balance being water.

9. The method of claim 1, wherein the post-treatment of step (3) comprises desulfurization, oil bathing, water washing, drying by baking, or a combination thereof.

10. An anti-bacteria, anti-mite, and/or anti-mould fabric, comprising the anti-bacterial, anti-mite, and/or anti-mould regenerated cellulose fiber prepared by the method of claim 1.

* * * * *